(12) United States Patent
Bourne et al.

(10) Patent No.: US 11,931,603 B2
(45) Date of Patent: Mar. 19, 2024

(54) RADIOTHERAPY APPARATUS

(71) Applicant: Elekta Limited, Crawley (GB)

(72) Inventors: Duncan Bourne, Sussex (GB); Per Bergfjord, East Grinstead (GB); Mikael Bergman, Sussex (GB)

(73) Assignee: Elekta Limited, Crawley (GB)

( * ) Notice: Subject to any disclaimer, the term of this patent is extended or adjusted under 35 U.S.C. 154(b) by 0 days.

(21) Appl. No.: 17/594,341

(22) PCT Filed: Apr. 9, 2020

(86) PCT No.: PCT/EP2020/060286
§ 371 (c)(1),
(2) Date: Oct. 12, 2021

(87) PCT Pub. No.: WO2020/208207
PCT Pub. Date: Oct. 15, 2020

(65) Prior Publication Data
US 2022/0184423 A1  Jun. 16, 2022

(30) Foreign Application Priority Data

Apr. 12, 2019 (GB) ..................... 1905243

(51) Int. Cl.
*A61N 5/10* (2006.01)
*A61N 5/00* (2006.01)

(52) U.S. Cl.
CPC ...... *A61N 5/1081* (2013.01); *A61N 2005/005* (2013.01)

(58) Field of Classification Search
None
See application file for complete search history.

(56) References Cited

U.S. PATENT DOCUMENTS

| 4,651,338 A | 3/1987 | Hahn |
| 5,299,249 A | 3/1994 | Burke et al. |

(Continued)

FOREIGN PATENT DOCUMENTS

| DE | 102013205606 A1 | 10/2014 |
| EP | 3466489 A1 | 4/2019 |
| WO | WO-2017220116 A1 | 12/2017 |

OTHER PUBLICATIONS

"International Application Serial No. PCT/EP2020/060286, International Search Report dated Jul. 3, 2020", (Jul. 3, 2020), 6 pgs.

(Continued)

*Primary Examiner* — Marcus H Taningco
(74) *Attorney, Agent, or Firm* — Schwegman Lundberg & Woessner, P.A.

(57) ABSTRACT

A radiotherapy apparatus including a rotatable gantry, a beam generation system, an on-gantry heat transfer system and an off-gantry heat transfer system is disclosed. The beam generation system is attached to the gantry and configured to generate abeam of therapeutic radiation. The on-gantry heat transfer system is configured to rotate with the gantry and includes a first conduit including a first thermally conductive surface, the on-gantry heat transfer system being configured to transfer heat generated by the beam generation system to the thermally conductive surface. The off-gantry heat transfer system includes a second thermally conductive surface, the off-gantry heat transfer system being configured to transfer heat away from the second thermally conductive surface. The first thermally conductive surface is in thermal contact with the second thermally conductive surface to form an interface between the on-gantry heat transfer system and the off-gantry heat transfer system, the interface comprising one of physical contact, or a gas bearing.

20 Claims, 10 Drawing Sheets

(56) References Cited

U.S. PATENT DOCUMENTS

| | | | |
|---|---|---|---|
| 5,610,968 A * | 3/1997 | Deucher | A61B 6/035 378/2 |
| 2015/0043706 A1 | 2/2015 | Mueller | |
| 2015/0320376 A1 | 11/2015 | Oishi | |
| 2018/0133518 A1 | 5/2018 | Harper et al. | |
| 2021/0255262 A1* | 8/2021 | Ni | A61B 5/055 |

OTHER PUBLICATIONS

"International Application Serial No. PCT/EP2020/060286, Written Opinion dated Jul. 3, 2020", (Jul. 3, 2020), 10 pgs.
"United Kingdom Application Serial No. 1919100.6, Search & Examination Report dated Jun. 23, 2020", (Jun. 23, 2020), 7 pgs.

* cited by examiner

RADIOTHERAPY APPARATUS

PRIORITY APPLICATIONS

This application is a U.S. National Stage Filing under 35 U.S.C. § 371 from International Application No. PCT/EP2020/060286, filed on Apr. 9, 2020, and published as WO2020/208207 on Oct. 15, 2020, which claims the benefit of priority to United Kingdom Application No. 1905243.0, filed on Apr. 12, 2019; the benefit of priority of each of which is hereby claimed herein, and which applications and publication are hereby incorporated herein by reference in their entirety.

This disclosure relates to radiotherapy apparatus, and in particular to radiotherapy apparatus comprising heat transfer systems.

BACKGROUND

Radiotherapy can be described as the use of ionising radiation, such as X-rays, to treat a human or animal body. Radiotherapy is commonly used to treat tumours within the body of a patient or subject. In such treatments, ionising radiation is used to irradiate, and thus destroy or damage, cells which form part of the tumour.

A radiotherapy device typically comprises a gantry which supports a beam generation system which is rotatable around a patient. For example, for a linear accelerator (linac) device, the beam generation system may comprise a source of radio frequency energy, a source of electrons, an accelerating waveguide, beam shaping apparatus, etc. Several components of such a linac device generate heat as they operate, for example transformers, magnets and the components of the beam generation system. Typically, a linac may generate several kWs of heat during beam-on.

It is known to use water cooling as part of a heat management system in a radiotherapy device. However, known systems are problematic for a number of reasons; they are complex and expensive, and are not well-suited for radiotherapy devices which comprise so-called 'continuously rotating' gantries, i.e. gantries which can be rotated 360 degrees around a patient. In known heat management systems for these continuously rotating gantry devices, water must be transported across a large diameter rotating joint. However, this technology is again complex, expensive, and is reliant on sliding seals which may develop leaks over time. In particular, these sliding seals are not well-suited for the large diameter bores which are required for modern radiotherapy devices.

In alternative known heat management system, heat is transferred away from the gantry into surrounding air using on-gantry fans. However, these systems are inefficient.

The present invention seeks to address these and other disadvantages encountered in the prior art.

SUMMARY

An invention is set out in the claims. The following summary comments should not be taken as limiting on the scope of the invention.

According to an aspect, there is provided a radiotherapy apparatus comprising a rotatable gantry and a beam generation system attached to the gantry configured to generate a beam of therapeutic radiation. The apparatus comprises an on-gantry heat transfer system configured to rotate with the gantry. The on-gantry heat transfer system comprises a first conduit comprising a first thermally conductive surface, and is configured to transfer heat generated by the beam generation system to the thermally conductive surface. The apparatus further comprises an off-gantry heat transfer system comprising a second thermally conductive surface, the off-gantry heat transfer system being configured to transfer heat away from the second thermally conductive surface. The first thermally conductive surface is in thermal contact with the second thermally conductive surface to form an interface between the on-gantry heat transfer system and the off-gantry heat transfer system. The interface may take a number of forms. For example, the interface may comprise direct physical contact, or a gas bearing.

The interface may comprise physical contact in that the surfaces touch one another. When the gantry rotates, the first thermally conductive surface may rotate with respect to, and slide against, the second thermally conductive surface. The interface may thus be called a sliding joint. The interface may alternatively comprise a gas bearing in that the first and second thermally conductive surfaces are separated via a film of gas which is maintained by a gas bearing.

FIGURES

Specific embodiments are now described, by way of example only, with reference to the drawings, in which.

FIGS. 4a-e depict various shapes and configurations of heat transferring conduits in accordance with the present disclosure.

Figure 5:
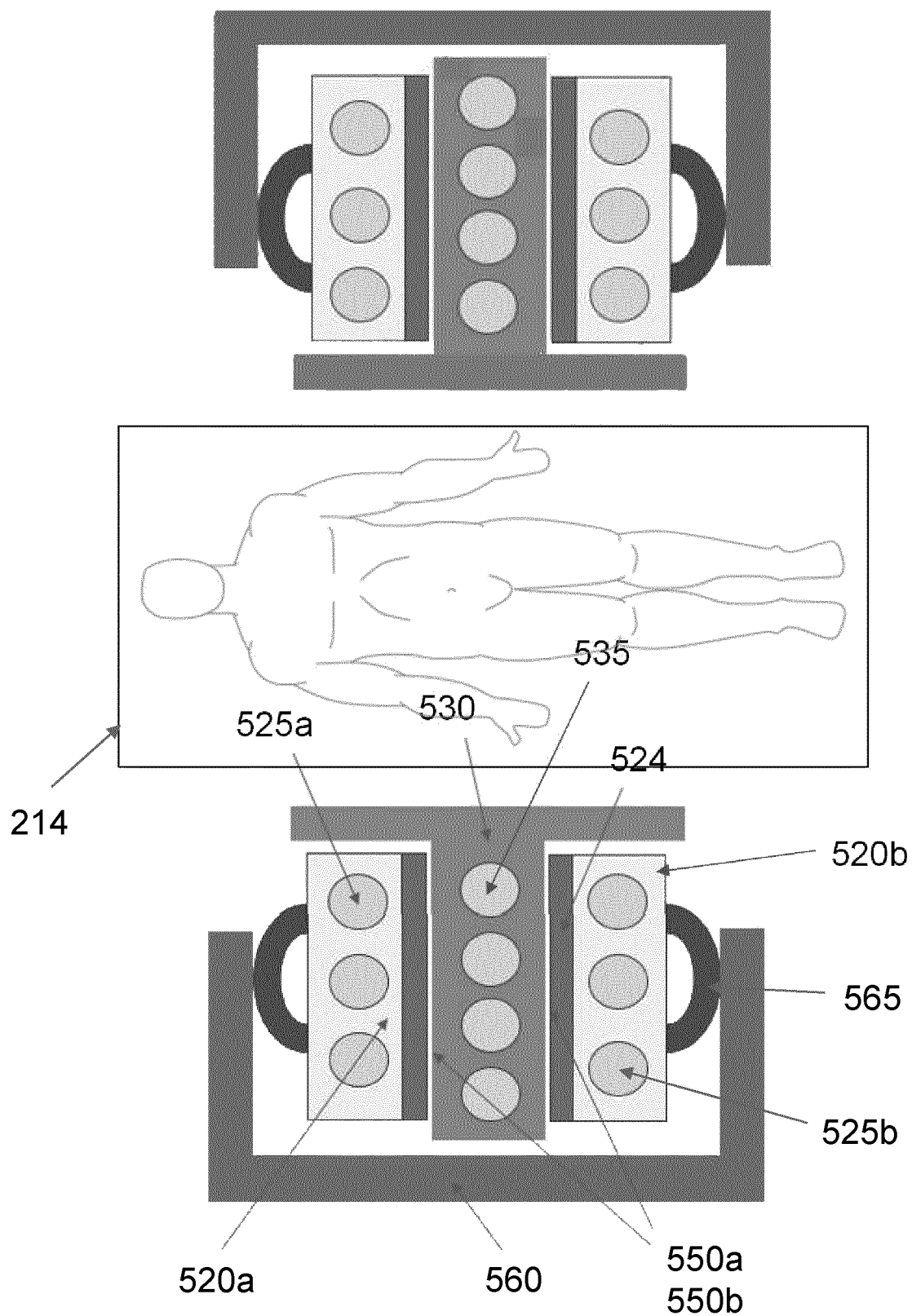

FIG. 5 depicts a rotor ring structure and first and second stator ring structures in accordance with the present disclosure.

Figure 6A:
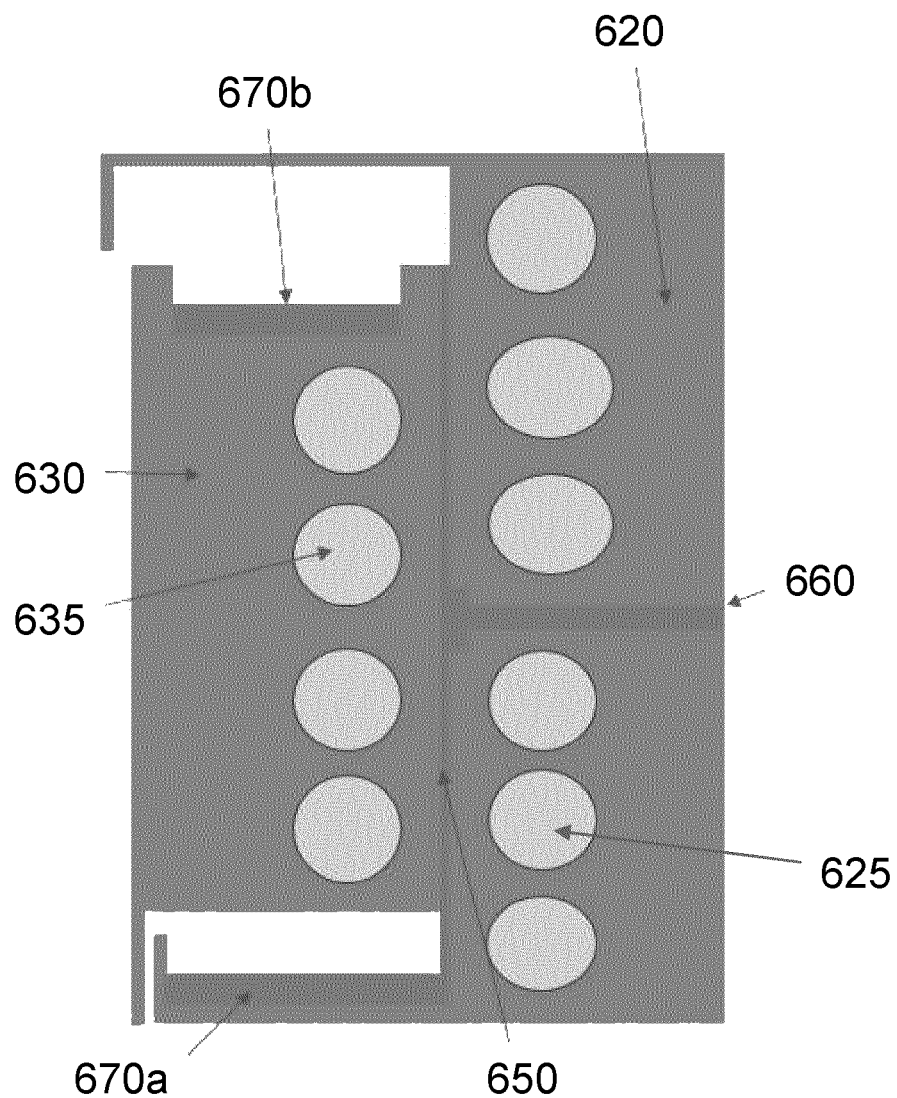

FIG. 6a depicts a rotor ring structure and a stator ring structure with lubricant feeds and drains in accordance with the present disclosure. The figure depicts a 'side-on' cross-section through part of the rotor ring structure and the stator ring structure, i.e. through an arc of each of the rotor ring structure and the stator ring structure.

Figure 6B:
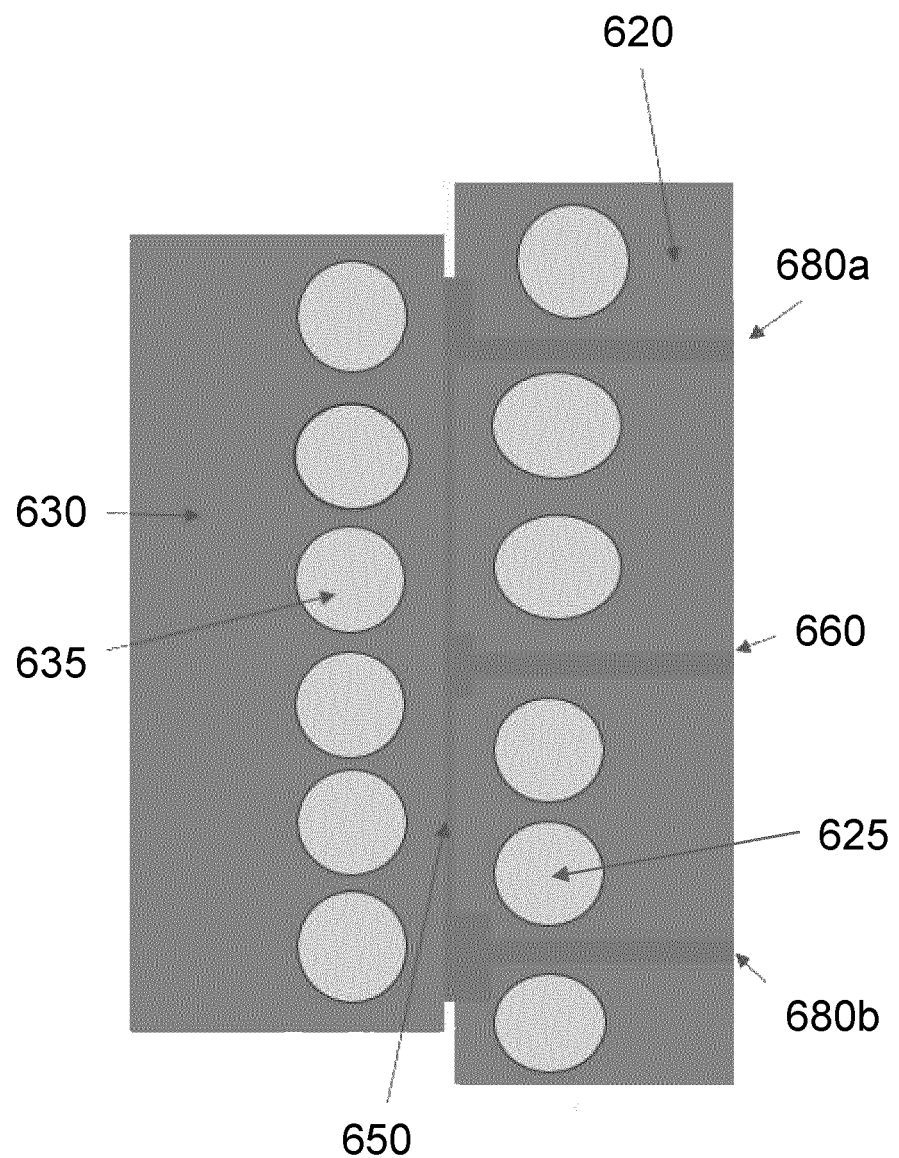

FIG. 6b depicts an alternative rotor ring structure and a stator ring structure with lubricant feeds and drains in accordance with the present disclosure. The figure depicts a 'side-on' cross-section through part of the rotor ring structure and the stator ring structure, i.e. through an arc of each of the rotor ring structure and the stator ring structure.

Figure 7:
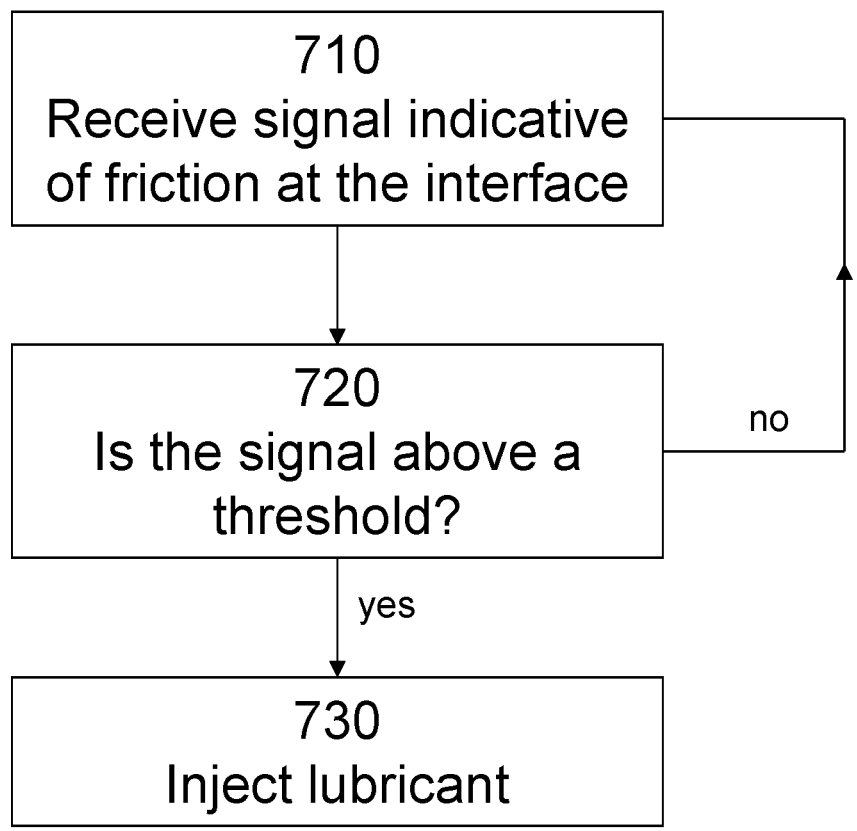

FIG. 7 depicts a method for injecting lubricant in accordance with the present disclosure.

DETAILED DESCRIPTION

Described broadly, the present application relates to an interface formed between a first thermally conductive surface forming part of an on-gantry heat transfer system, and a second thermally conductive surface forming part of an off-gantry heat transfer system. The thermally conductive surfaces may be surfaces of respective conduits or pipes, though they need not be so. The form of the interface may take several forms. The interface may be one of direct physical contact, which may be described as a sliding interface as the gantry is configured to rotate with respect to the off-gantry heat transfer system.

Figure 1:
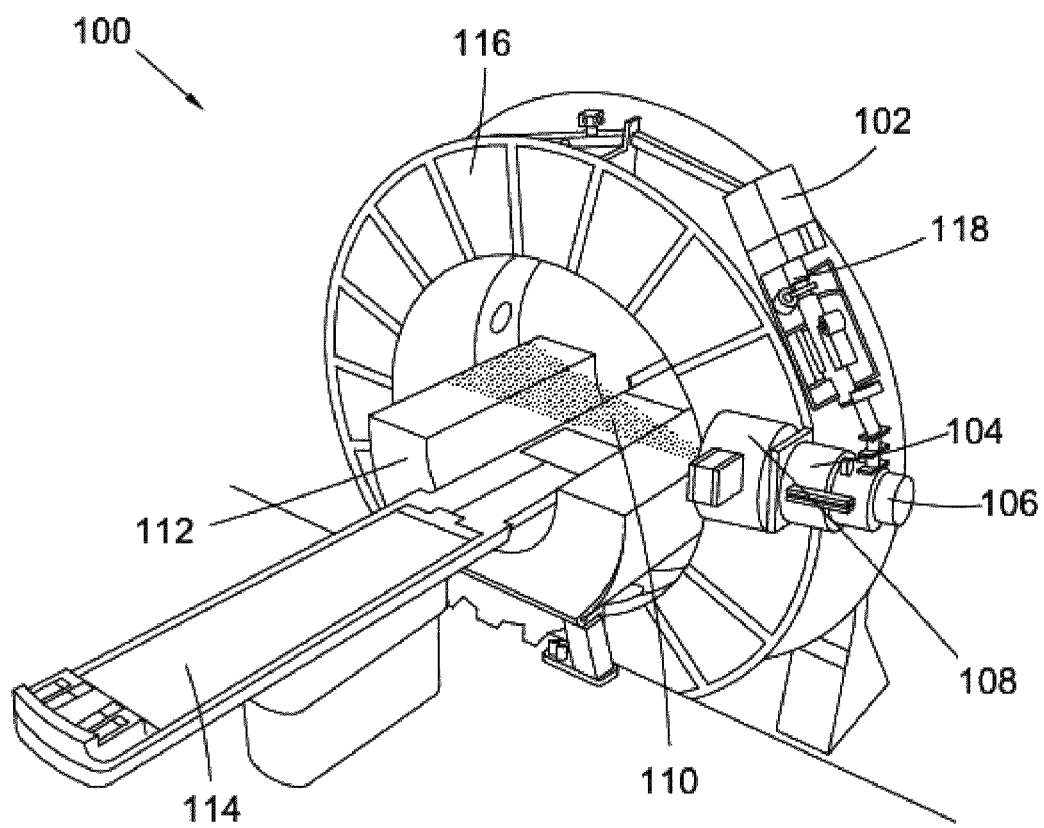
FIG. 1 depicts a radiotherapy device or apparatus according to the present disclosure.

FIG. 1 depicts a radiotherapy device suitable for delivering, and configured to deliver, a beam of radiation to a patient during radiotherapy treatment. The device and its constituent components will be described generally for the purpose of providing useful accompanying information for the present invention. The device depicted in FIG. 1 is in accordance with the present disclosure and is suitable for use with the disclosed systems and apparatuses. While the device in FIG. 1 is an MR-linac, the implementations of the present disclosure may be any radiotherapy device, for example a linac device.

The device depicted in FIG. 1 is an MR-linac. The device comprises both MR imaging apparatus 112 and radiotherapy (RT) apparatus which may comprise a linac device. In operation, the MR scanner produces MR images of the patient, and the linac device produces and shapes a beam of radiation and directs it toward a target region within a patient's body in accordance with a radiotherapy treatment plan. The depicted device does not have the usual 'housing' which would cover the MR imaging apparatus 112 and RT apparatus in a commercial setting such as a hospital.

The MR-linac device depicted in FIG. 1 comprises a source of radiofrequency waves 102, a waveguide 104, a source of electrons (not shown), a source of radiation 106, a collimator 108 such as a multi-leaf collimator configured to collimate and shape the beam, MR imaging apparatus 112, and a patient support surface 114. The device also comprises a housing which, together with the ring-shaped gantry defines a bore. The moveable support surface 114 can be used to move a patient, or other subject, into the bore when an MR scan and/or when radiotherapy is to commence. The MR imaging apparatus 112, RT apparatus 120, and a subject support surface actuator are communicatively coupled to a controller or processor. The controller is also communicatively coupled to a memory device comprising computer-executable instructions which may be executed by the controller.

The RT apparatus comprises a source of radiation 106 and a radiation detector (not shown). Typically, the radiation detector is positioned diametrically opposed to the radiation source 106. The radiation detector is suitable for, and configured to, produce radiation intensity data. In particular, the radiation detector is positioned and configured to detect the intensity of radiation which has passed through the subject. The radiation detector may also be described as radiation detecting means, and may form part of a portal imaging system.

The radiation source 106 defines the point at which the treatment beam 110 is introduced into the bore. The radiation source 106 forms part of a beam generation system, which may comprise a source of RF energy 102, an electron gun, and a waveguide 104. The beam generation system is attached to the rotatable gantry 116 so as to rotate with the gantry 116. In this way, the radiation source 106 is rotatable around the patient so that the treatment beam 110 can be applied from different angles around the gantry 116. In a preferred implementation, the gantry is continuously rotatable. In other words, the gantry can be rotated by 360 degrees around the patient, and in fact can continue to be rotated past 360 degrees. The gantry may be ring-shaped. In other words, the gantry may be a ring-gantry.

The source 102 of radiofrequency waves, such as a magnetron, is configured to produce radiofrequency waves. The source 102 of radiofrequency waves is coupled to the waveguide 104 via circulator 118, and is configured to pulse radiofrequency waves into the waveguide 104. Radiofrequency waves may pass from the source 102 of radiofrequency waves through an RF input window and into an RF input connecting pipe or tube. A source of electrons (not shown), such as an electron gun, is also coupled to the waveguide 104 and is configured to inject electrons into the waveguide 104. In the source of electrons, electrons are thermionically emitted from a cathode filament as the filament is heated. The temperature of the filament controls the number of electrons injected. The injection of electrons into the waveguide 104 is synchronised with the pumping of the radiofrequency waves into the waveguide 104. The design and operation of the radiofrequency wave source 102, electron source and the waveguide 104 is such that the radiofrequency waves accelerate the electrons to very high energies as the electrons propagate through the waveguide 104.

The design of the waveguide 104 depends on whether the linac accelerates the electrons using a standing wave or travelling wave, though the waveguide typically comprises a series of cells or cavities, each cavity connected by a hole or 'iris' through which the electron beam may pass. The cavities are coupled in order that a suitable electric field pattern is produced which accelerates electrons propagating through the waveguide 104. As the electrons are accelerated in the waveguide 104, the electron beam path is controlled by a suitable arrangement of steering magnets, or steering coils, which surround the waveguide 104. The arrangement of steering magnets may comprise, for example, two sets of quadrupole magnets.

Once the electrons have been accelerated, they may pass into a flight tube. The flight tube may be connected to the waveguide by a connecting tube. This connecting tube or connecting structure may be called a drift tube. The electrons travel toward a heavy metal target which may comprise, for example, tungsten. Whilst the electrons travel through the flight tube, an arrangement of focusing magnets act to direct and focus the beam on the target.

To ensure that propagation of the electrons is not impeded as the electron beam travels toward the target, the waveguide 104 is evacuated using a vacuum system comprising a vacuum pump or an arrangement of vacuum pumps. The pump system is capable of producing ultra-high vacuum (UHV) conditions in the waveguide 104 and in the flight tube. The vacuum system also ensures UHV conditions in the electron gun. Electrons can be accelerated to speeds approaching the speed of light in the evacuated waveguide 104.

The source of radiation 106 is configured to direct a beam 110 of therapeutic radiation toward a patient positioned on the patient support surface 114. The source of radiation 106 may comprise a heavy metal target toward which the high energy electrons exiting the waveguide are directed. When the electrons strike the target, X-rays are produced in a variety of directions. A primary collimator may block X-rays travelling in certain directions and pass only forward travelling X-rays to produce a treatment beam 110. The X-rays may be filtered and may pass through one or more ion chambers for dose measuring. The beam can be shaped in various ways by beam-shaping apparatus, for example by using a multi-leaf collimator 108, before it passes into the patient as part of radiotherapy treatment.

In some implementations, the source of radiation 106 is configured to emit either an X-ray beam or an electron particle beam. Such implementations allow the device to provide electron beam therapy, i.e. a type of external beam therapy where electrons, rather than X-rays, are directed toward the target region. It is possible to 'swap' between a first mode in which X-rays are emitted and a second mode in which electrons are emitted by adjusting the components of the linac. In essence, it is possible to swap between the first and second mode by moving the heavy metal target in or out of the electron beam path and replacing it with a so-called 'electron window'. The electron window is substantially transparent to electrons and allows electrons to exit the flight tube.

The subject or patient support surface 114 is configured to move between a first position substantially outside the bore, and a second position substantially inside the bore. In the first position, a patient or subject can mount the patient support surface. The support surface 114, and patient, can then be moved inside the bore, to the second position, in order for the patient to be imaged by the MR imaging apparatus 112 and/or imaged or treated using the RT apparatus. The movement of the patient support surface is effected and controlled by a subject support surface actuator, which may be described as an actuation mechanism. The actuation mechanism is configured to move the subject support surface in a direction parallel to, and defined by, the central axis of the bore. The terms subject and patient are used interchangeably herein such that the subject support surface can also be described as a patient support surface. The subject support surface may also be referred to as a moveable or adjustable couch or table.

The radiotherapy apparatus/device depicted in FIG. 1 also comprises MR imaging apparatus 112. The MR imaging apparatus 112 is configured to obtain images of a subject positioned, i.e. located, on the subject support surface 114. The MR imaging apparatus 112 may also be referred to as the MR imager. The MR imaging apparatus 112 may be a conventional MR imaging apparatus 110 operating in a known manner to obtain MR data, for example MR images. The skilled person will appreciate that such a MR imaging apparatus 112 may comprise a primary magnet, one or more gradient coils, one or more receive coils, and an RF pulse applicator. The operation of the MR imaging apparatus is controlled by the controller.

The controller is a computer, processor, or other processing apparatus. The controller may be formed by several discrete processors; for example, the controller may comprise an MR imaging apparatus processor, which controls the MR imaging apparatus 110; an RT apparatus processor, which controls the operation of the RT apparatus; and a subject support surface processor which controls the operation and actuation of the subject support surface. The controller is communicatively coupled to a memory, i.e. a computer readable medium.

The linac device also comprises several other components and systems as will be understood by the skilled person. For example, in order to ensure the linac does not leak radiation, appropriate shielding is also provided.

Figure 2:
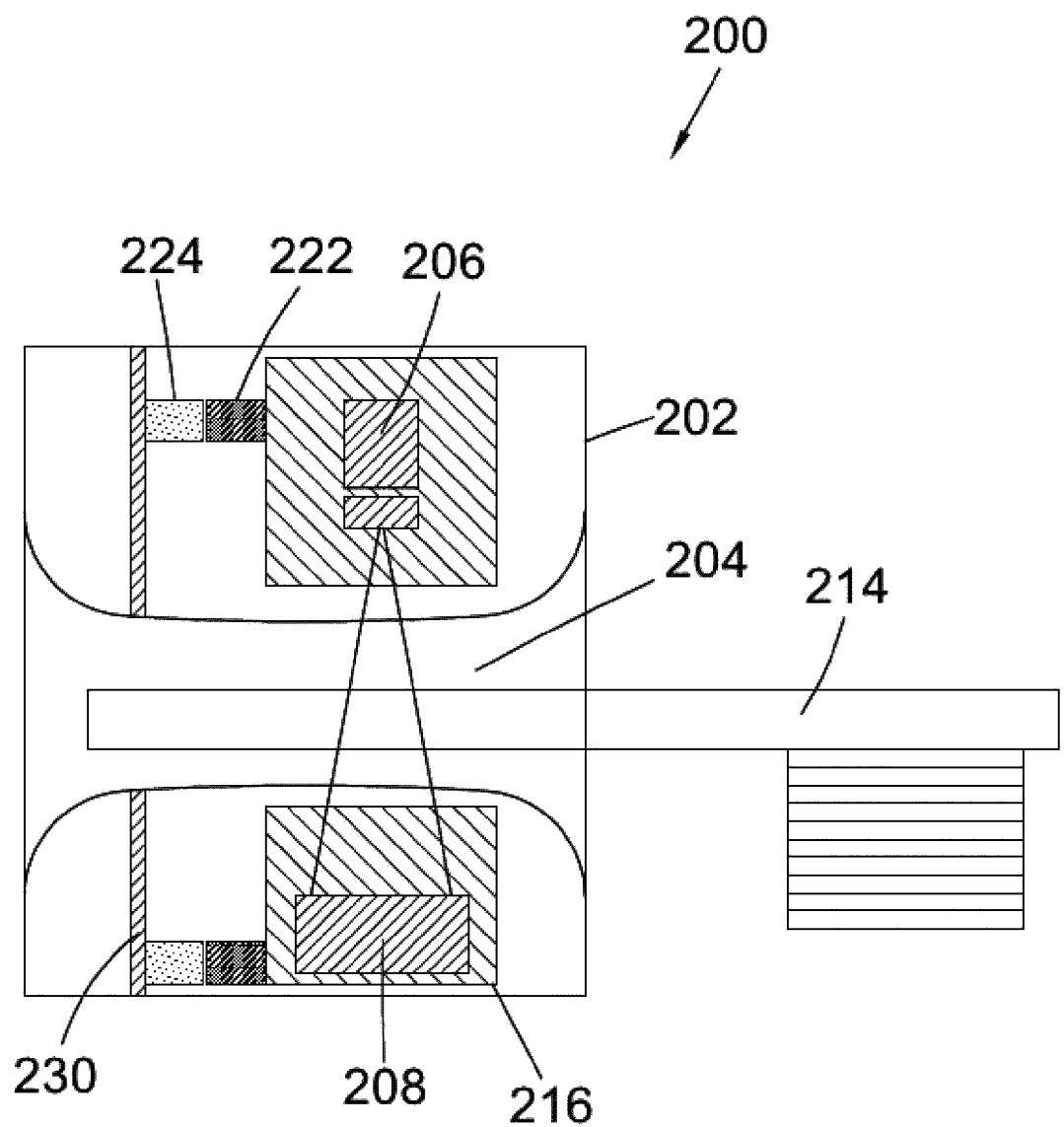
FIG. 2 depicts a cross-section through a radiotherapy device or apparatus according to the present disclosure.

FIG. 2 shows a cross-section through a radiotherapy device or apparatus 200 according to the present disclosure. The device may be in accordance with the device 100 depicted generally in FIG. 1. The cross-section is along a plane which incorporates a rotation axis of the gantry 216. The apparatus may be any type of radiotherapy device, for example a linac device or an MR-linac as described generally above in relation to FIG. 1.

The radiotherapy device 200 comprises a housing 202 which houses the gantry 216. The gantry 216 and housing 202 together define a bore 204. A patient support surface 214 is operable to move a patient in to and out from the bore in a known manner and as described above in relation to FIG. 1. The device 200 comprises a source of radiation 206 attached to the gantry 216. The gantry is rotatable about a gantry rotation axis such that the radiation source 206 may be rotated to supply radiation from various angles around a patient. In addition to the radiation source 206, additional beam generation equipment (not shown) is also attached to the gantry. The radiation source and other beam generation equipment together form a beam generation system. The beam generation system may comprise several components such as a magnetron, electron gun, waveguide, beam directing magnets, modulator, target, circulator etc. as described generally above in relation to FIG. 1. The beam generation system is attached to the gantry and configured to rotate with the gantry. The gantry also carries several electronic components, for example a control system operable to control the operation of the various on-gantry components.

These 'on-gantry' components, i.e. components located on the gantry and configured to rotate with the gantry of the device 200, generate heat during operation. According to the present disclosure, to ensure the radiotherapy device 200 continues to operate in an optimal manner and within optimal temperature parameters, heat is transferred away from these on-gantry components via an interface between an on-gantry heat transfer system and an off-gantry heat transfer system.

Generally speaking, the on-gantry heat transfer system is configured to transfer heat from one or more components located on the gantry, for example those components that comprise the beam generation system, to a thermally conductive surface of a first conduit 222. The components which comprise the on-gantry heat transfer system are attached to the gantry and/or are configured to rotate with the gantry. The on-gantry heat transfer system comprises the first conduit 222 which has a first thermally conductive surface. The on-gantry heat transfer system also comprises a system or network of ducts and/or additional fluid conduits which pass through, or near, heat-generating components located on the gantry such as those components which comprise the beam generation system. Fluid is pumped through the on-gantry heat transfer system by a pump or other fluid regulator. Heat generated by the on-gantry components is transferred into the fluid, which in turn is pumped around the on-gantry heat transfer system. In this way, the ducting system of the on-gantry heat transfer system thermally couples at least one heat-generating on-gantry component with the first conduit 222.

In a preferred implementation, the first conduit 222 is ring-shaped, or substantially ring-shaped. The first conduit 222 may therefore be described as a first annular conduit. The pipe which forms the first conduit 222 may have a square or rectangular-shaped cross section as can be appreciated from FIG. 2. Fluid from the on-gantry heat transfer system, which has been heated by on-gantry components, passes into the first conduit 222 via a first aperture (not shown). The first conduit 222 comprises a first thermally conductive surface. The fluid is pumped around, or through, the first conduit 222, and heat is transferred from the fluid to the first thermally conductive surface. Fluid exits the first conduit 222 via a second aperture (not shown) for re-circulation back through the system of ducts and/or additional fluid conduits, thus providing cooled fluid which is better able to accept heat from the heat-generating on-gantry components.

Figure 3:
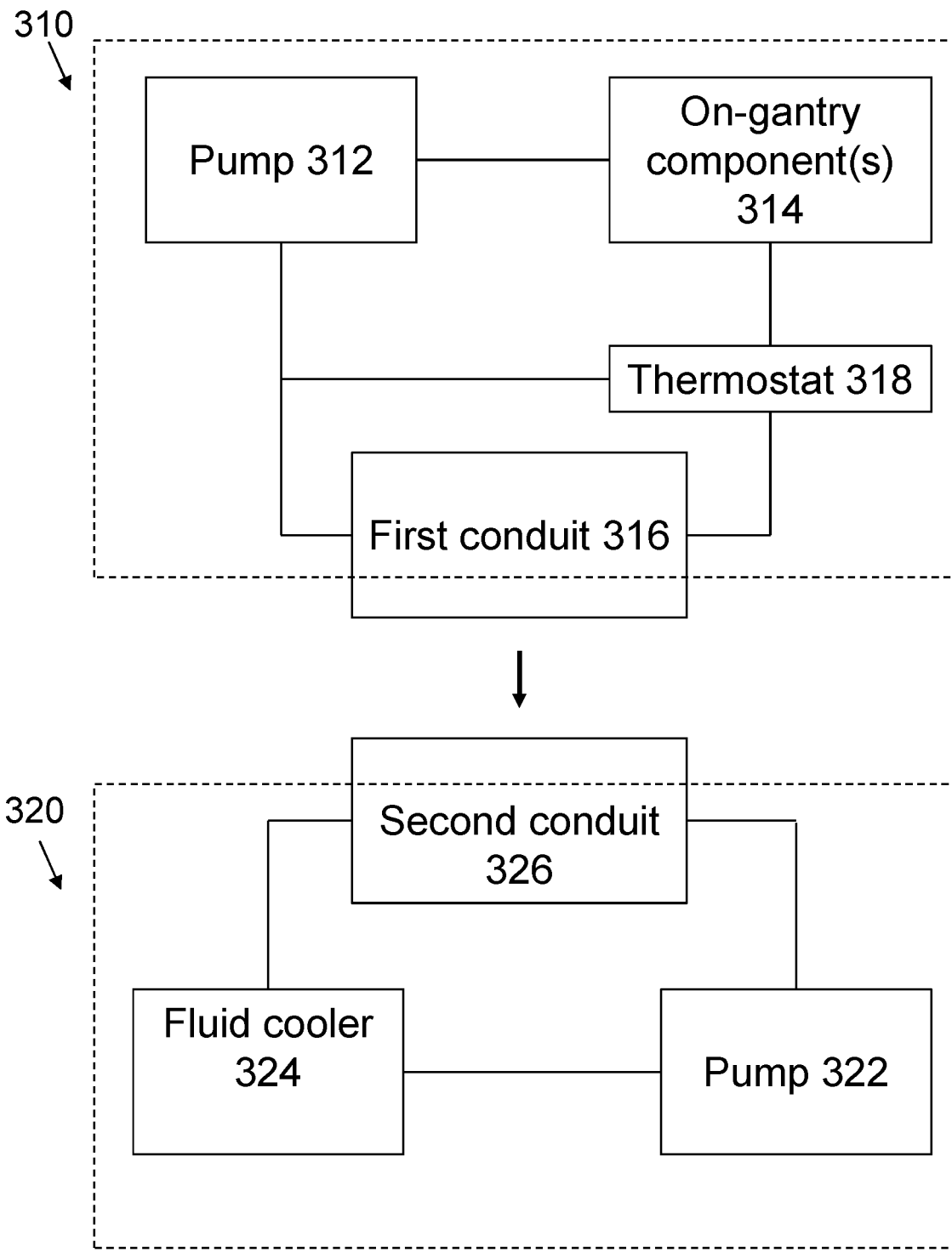
FIG. 3 depicts a schematic diagram showing the interface between an on-gantry heat transfer system and an off-gantry heat transfer system.

As will be described in greater detail with respect to FIG. 3, the degree to which fluid from the on-gantry heat transfer system is passed through the first conduit 222, rather than re-circulated through the system of ducts and back to the on-gantry components, is controlled via a thermostat. The thermostat may comprise a valve which opens to varying degrees based on the temperature of the fluid.

The off-gantry heat transfer system comprises a second thermally conductive surface, and is configured to transfer heat away from the second thermally conductive surface. The off-gantry heat transfer system is comprised of a number of components which are located off the gantry, i.e. not on the gantry. These components do not rotate with the gantry. In other words, the gantry is configured to rotate with respect to the off-gantry heat transfer system. The off-gantry heat transfer system comprises a second conduit 224. The second conduit 224 comprises the second thermally conductive surface.

In a preferred implementation, the second conduit 224 is ring-shaped, or substantially ring-shaped. The second conduit 224 may therefore be described as a second annular conduit. The pipe which forms the second conduit 224 may also have a square or rectangular-shaped cross section. The second conduit may have a shape and form which corresponds with that of the first conduit. Because the second conduit 224 does not rotate with the gantry, it may be described as a stator ring and/or a stator conduit, while the first conduit 222 may be referred to as a rotor ring and/or a rotor conduit.

The device 200 comprises a stator structure 230. The stator structure 230 may be described as a support structure or a frame. The stator structure is an element of the radiotherapy device 200 which does not rotate as the gantry rotates. In other words, the gantry 216 is configured to rotate with respect to the stator structure. The stator structure 230 supports, houses, holds, or otherwise comprises the second conduit 224. The stator structure may form part of the housing 202.

The off-gantry heat transfer system comprises a pump or regulator which pumps fluid around the off-gantry heat transfer system. The off-gantry heat transfer system also comprises a fluid cooler. The fluid cooler may comprise a heat sink, and/or an external thermal system to which heat from the fluid can be transferred via, for example, a heat exchanger. The fluid cooler may be located outside the bunker in which the radiation apparatus is located.

The first thermally conductive surface of the first conduit 222 is in thermal contact with the second thermally conductive surface of the second conduit 224 to form an interface between the on-gantry heat transfer system and the off-gantry heat transfer system. The interface allows heat to be exchanged between the on-gantry heat transfer system and the off-gantry heat transfer system. Together, the first conduit 222 and the second conduit 224 comprise a heat exchanger. The conduits may be described as heat exchanging elements. As can be seen from FIG. 2, the first conduit 222 faces the second conduit 224 to form the interface. More particularly, the first thermally conductive surface of the first conduit 222 faces, mates, and/or is coupled with the second conductive surface of the second conduit 224. The conduits are thus in thermal contact, and in a preferred implementation are also in direct physical contact. Such an implementation maximises the heat that can be transferred from the first conduit 222 to the second conduit 224. As the first conduit 222 rotates with respect to the second conduit, the first conduit 222 slides against the second conduit 224 and thus the first and second conduits 222, 224 are coupled via a sliding joint. In this implementation, the interface between the on and off-gantry heat transfer systems is a sliding interface.

The surfaces, i.e. the first and second thermally conductive surfaces, which face each other to form the interface may be biased together via biasing means (not shown). The first and second conduit 222, 224 may be biased together via the biasing means. The biasing means may be described as a biasing mechanism, biasing arrangement, or a spring assembly. The biasing mechanism may comprise an arrangement of springs configured to bias the first conduit 222 toward the second conduit 224, and/or the second conduit 224 toward the first conduit 222. The spring/biasing force provided by the biasing system should be as light as possible, as this will reduce the friction between the surfaces and hence reduce power loss, wear and heat generation. Only a few g of force is required, which represents only around 100 W of heat generated by friction. In a system designed to transfer 10 kW, as is typical for radiotherapy systems, this frictional heat is insignificant.

The biasing means may comprise an arrangement of biasing members, such as springs, located between the stator structure 230 and the second conduit. The springs could be any form of suitable springs, such as torsion springs. In implementations where the second conduit is ring-shaped, the biasing members may be located around the circumference of the second conduit. For example, the biasing means may comprise a particular number of biasing members spaced evenly around the circumference of the ring-shaped, or substantially ring-shaped, second conduit 224 between the stator structure 230 and the second conduit 224.

The biasing members may additionally or alternatively be placed between a second stator structure (not shown) and the stator structure 230. In other words, there could be another stationary structure facing and/or located behind the stator structure 230 which serves to provide a surface on which biasing members may be placed in order that the stator structure 230, and hence the second conduit 224, is biased toward the first conduit 222. In another implementation, the biasing members may additionally or alternatively be placed between the first conduit 222 and the gantry 206 in order to bias the first conduit 222 toward the second conduit 224.

Alternatively, the stator structure 230 may form the biasing means. In such an implementation, the stator structure comprises a resilient material which can flex, for example, in a direction parallel with the gantry rotation axis. The stator structure may be anchored at a location near its inner circumference. In this way, the stator structure provides an inherent biasing mechanism and acts to bias the second conduit 224 toward the first conduit 222.

In implementations in which the first and second conduit 222, 224 are coupled via physical contact with one another, a thermally conductive lubricant may be provided between the first and second thermally conductive surfaces. This lubricant may be provided via lubricant provision means, such as a fitting e.g. a grease fitting, or grease nipple. Such fittings are known and operate to facilitate the application of lubrication, or act to autonomously provide lubrication, to the interface.

The components which comprise the on-gantry and off-gantry heat transfer systems will be described in more detail in relation to FIG. 3, which depicts a simplified schematic diagram of the components of each system.

The on-gantry heat transfer system 310 comprises a pump 312, at least one on-gantry component 314 that generates heat as it operates, a thermostat 318, and a first conduit 316. These components of the on-gantry heat transfer system 310 are linked by a suitable network or system of ducts and/or additional fluid conduits. The pumps 312, 322 may equivalently be pumping systems or other fluid regulators. The at least one on-gantry component 314 may be a plurality of on-gantry components, for example those components which form the beam generation system as discussed above.

The off-gantry heat transfer system 320 comprises a pump 322, a fluid cooler 324, and a second conduit 326. The fluid cooler 324 is configured to cool the fluid pumped around the off-gantry heat transfer system, i.e. is configured such that heat is transferred from the fluid to the fluid cooler 324. The on-gantry and off-gantry heat transfer systems may each comprise closed circuits for the circulation of fluid. The fluid cooler 324 may be a hospital heating, ventilation and air condition (HVAC) system. Alternatively or additionally, the fluid cooler 324 may comprise a heat exchanger of any form, for example one configured to provide cooling via liquid nitrogen. The fluid cooler 324 may also comprise any of a number of configurations of heat sink.

During operation of the radiotherapy device 200, the gantry 216, and therefore the on-gantry heat transfer system 310, rotates with respect to the off-gantry heat transfer system 320. Heat is generated in the at least one on-gantry component 314 as the component 314 operates. For example, as the magnetron operates to produce radiofrequency waves, heat is generated which must be transported away from the magnetron. This heat is transferred into the fluid being pumped around the on-gantry heat transfer system 310. While the fluid has a temperature under a particular 'threshold' temperature, the thermostat 318 remains closed and fluid is recirculated to the on-gantry component(s).

The thermostat 318 operates to regulate the temperature of the fluid and, hence operates to regulate temperature of the on-gantry component(s) 314. As the fluid heats up, the thermostat 318 gradually opens and connects in the first conduit 316. In other words, the thermostat controls to what degree fluid is passed through a fluid circuit which incorporates the first conduit 316. At low temperatures the first aperture, through which fluid flows into the first conduit, may be completely closed. The thermostat valve opens by an increasing degree as the temperature of the fluid increases. In this way, the temperature of the fluid is maintained roughly at a constant temperature, whether the system is rotating, radiating or not.

The thermostat may be a mechanical thermostat comprising a wax thermostatic element or a memory metal, or may be a more complex system comprising a temperature sensor coupled with a controller configured to adjust a variable valve based on signals from the sensor. The skilled person would understand that different forms of thermostat may be used.

The thermostat 318 may include a shunt valve or a controlled shunt device. The shunt valve may be controlled, for example, via a computer or processor which receives signals from one or more on-gantry temperature sensors. These temperature sensors can be disposed at on-gantry locations which are particularly sensitive to high temperatures or variations in temperature or are particularly likely to experience high temperatures or variations in temperature. For example, these temperature sensors could be collocated with one or more of the on-gantry components 314. For example, the beam generation system may need to be tuned very accurately and may require a stable temperature in order to generate a beam according to desired parameters. Therefore, a temperature sensor may be collocated with the beam generation system. These temperature sensors are configured to provide signals indicative of the temperature of the on-gantry coolant. These signals can be transmitted from the temperature sensors to the shunt valve. The shunt valve can be driven to open or close to a specified degree based on the signals, for example using a motorized servo-system. This can enable the temperature to be controlled very accurately, for example to within plus or minus 0.1° C.

When the shunt valve is fully closed, the on-gantry coolant passes around an on-gantry loop, e.g. through the on-gantry component(s) 314 and/or through the fluid conduits passing nearby the on-gantry heat transfer component(s) 314, through connecting fluid conduits to the pump 312, and back to the on-gantry component(s) 314. None of the on-gantry coolant passes to the heat transfer surface(s) 316. As the shunt valve opens, the on-gantry coolant flows to the heat transfer surface(s) 316. The degree to which the shunt valve is opened controls the degree to which on-gantry coolant passes to the heat transfer surface(s) 316. When the shunt valve is in its most open state, most or all flow of the on-gantry coolant passes through the heat transfer surface(s) 316. The shunt valve may be opened to an extent that enables a stable temperature to be maintained. The shunt valve can therefore be seen as throttling between two extremes: the valve being fully closed in which no on-gantry coolant passes to the heat transfer surface(s) 316, and being in its most open state in which most or all of the on-gantry coolant passes to the heat transfer surface(s) 316.

In some implementations, the computer which controls the shunt valve also controls the pump 312. The computer or other controller, which may be an on-gantry controller, increases the pumping rate of the pump 312 to account for the pressure drop in the on-gantry heat transfer system 310 when the shunt valve is opened. By varying the pump speed based on the degree to which the shunt valve is open, it is possible to obtain a constant flow rate over the heat transfer surface 316. This helps to ensure the temperature of the on-gantry coolant, and thus the temperature of the on-gantry component(s) 314, is kept constant. The shunt valve can thus be operated to obtain and maintain a desirable on-gantry coolant temperature, and the pump 312 can be operated to account for increases and decreases in the system pressure following operation of the shunt valve. Alternatively, or in addition, the pump speed may be varied based on the degree to which the shunt valve is open in order to maintain a constant flow of coolant past the on-gantry component(s) 314. Maintaining this flow enables stable temperatures of the on-gantry components 314 to be achieved.

As discussed above, the first conduit 316 and second conduit 326 together form a heat exchanger. As fluid passes through the first conduit 316, heat is transferred to the second conduit 326 from the first conduit 316. More particularly, heat is transferred from the fluid pumped around the on-gantry heat transfer system, to the first conductive surface of the first conduit 222, and then to the second conductive surface of the second conduit 224. The heat is then transferred from the second conductive surface of the second conduit 326, to the fluid being pumped around the off-gantry heat transfer system 320, and is then transferred out of the off-gantry heat transfer system via the fluid cooler 324.

The interface between the first conduit 316 and second conduit 326 can take a number of forms. In each implementation, the conduits are in thermal contact with one another. In other words, heat can be transferred between the conduits such that they form a heat exchanger. In preferred implementations, there is no need for a fan or other system to assist or effect the heat exchange.

The first and second conduit are comprised of a thermally conductive material. In particular, the first and second thermally conductive surfaces are comprised of thermally conductive material. To maximise the surface area over which the two conduits are in thermal contact and to minimise friction, the first and second thermally conductive surfaces may be flat, and in a preferred implementation are also smooth. This can be achieved using square-section pipe as depicted in FIG. 2. The smooth and flat surfaces (i.e. the first and second thermally conductive surfaces) of the first and second conduit which face each other to form the interface may, in a preferred implementation, be manufactured via diamond turning. The conduits may be copper or brass tubes. These materials are particularly beneficial due to their thermal conductivity and relative ease of forming.

The conduits may be fitted into recesses in two respective separation platters. A first such platter may house, hold, support or otherwise comprise the first conduit, and in turn this first platter is mounted to the gantry. Conversely, a second platter which houses, holds, supports or otherwise comprises the second conduit is mounted to the stator structure. These platters are comprised of a thermally insulating material such as polyurethane, and act to ensure heat is not transferred to surrounding structure within the housing of the radiotherapy device. The separation platter may equally be referred to as a separation disc, element, or component.

The fluid used in both heat transfer systems may be any suitable fluid, for example water. The fluid may comprise water, inhibiting chemicals to inhibit the growth of mould, anti-freeze agents, and other beneficial chemicals.

In a preferred implementation, each of the first and the second conduit are ring-shaped. The rings are of equal or substantially equal diameter and are configured and positioned such that they align with one another. Such an interface, i.e. one which is formed via the thermal coupling of two substantially annular or ring-shaped heat transfer surfaces, elements, or conduits, is particularly advantageous for a radiotherapy device comprising a rotating gantry, and in particular is advantageous for a device comprising a continuously rotating gantry configured to rotate 360 degrees around a patient.

In such a radiotherapy device, the gantry can continuously rotate while the hot rotor ring (first conduit) maintains face-to-face contact with the cold ring (second conduit). Heat is transferred efficiently regardless of gantry angle or speed of rotation.

In a preferred implementation, the first and second thermally conductive surfaces are in direct contact with one another. In other words, the interface comprises direct physical contact. Such an interface is particularly advantageous as it allows the efficient transfer of heat from the on-gantry heat transfer system to the off-gantry heat transfer system.

As mentioned in the background section, a known heat transfer system operates via a rotary union in which hot fluid is transferred from an inner 'core' to an outer core. However, these rotary unions are prone to leak fluid from the seals. These rotary unions must be very large to accommodate the bore of the radiotherapy device, and this puts a large amount of drag force/stress on the seals. These known devices are heavy, complex, and generate a lot of noise as they operate which is creates an adverse effect on patient comfort. The use of an interface between two thermally conductive surfaces which comprises direct physical contact, or an air bearing, in the manner described herein addressed these problems as it is a simpler mechanism to implement, produces less noise, and is not prone to fluid leaks.

It will be understood that the above description of specific embodiments is by way of example only and is not intended to limit the scope of the present disclosure. Many modifications of the described embodiments, some of which are now described, are envisaged and intended to be within the scope of the present disclosure.

FIGS. 4a-4d show different implementations and configurations of heat transfer conduits 420, such as one of the first and second conduits described herein, according to the present disclosure. Each conduit 420 is shown embedded within a separation platter 410. The purpose of these figures is to show possible implementations of the concepts of the present disclosure. The described features and configurations may be used with each other and the disclosed features are interchangeable between described implementations. For example, features shown and described primarily in relation to one of the figures may be used with an implementation described primarily with respect to another figure. While reference is made to a separation platter, reference numeral 410 may depict any supporting structure configured to support and/or hold the conduits.

The platters and conduits shown in FIGS. 4a-e may form part of either the on or off-gantry heat transfer system. If the platter and conduit are to form part of the on-gantry heat transfer system, water that has been heated by on-gantry components passes through a first aperture 430 and is pumped around the conduit to exit through a second aperture 440 for re-circulation back to the on-gantry components in the manner described generally above. Similarly, if the conduit 420 and platter 410 are to form part of the off-gantry heat transfer system, water that has been cooled by the fluid cooler will flow into the first aperture 430 and will be pumped around the ring to exit through the second aperture 440 for re-circulation back to the fluid cooler.

Figure 4A:
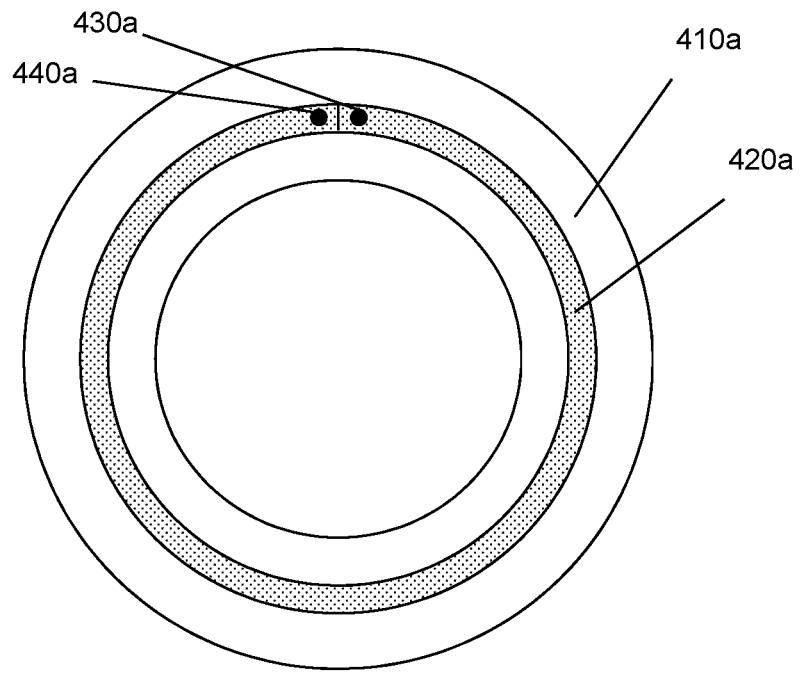

With reference to FIG. 4a, the separation platter comprises a ring-shaped groove or recess into which the heat transfer conduit 420a is embedded. In the particular implementation shown, the platter 420a is annular, as is the heat transfer conduit 420a. The heat transfer conduit 420a comprises a first aperture 430a, through which fluid can enter the conduit 420a, and a second aperture 440a through which fluid can exit the heat transfer conduit 420a. Fluid is pumped into the conduit via the inlet aperture 430a, is pumped around the circumference of the ring, and exits the conduit via exit aperture 440a. The inlet aperture 430a may be separate from the outlet aperture 440a via a disruption in the conduit, or the conduit may be continuous (as shown explicitly in FIG. 4e). The platter 410a also comprises apertures which are located and sized so as to correspond with the first and second apertures 430a 440a to allow connection of the conduit 420a to the duct network and/or additional fluid conduits of the off or on-gantry heat transfer system as described generally above.

Figure 4B:
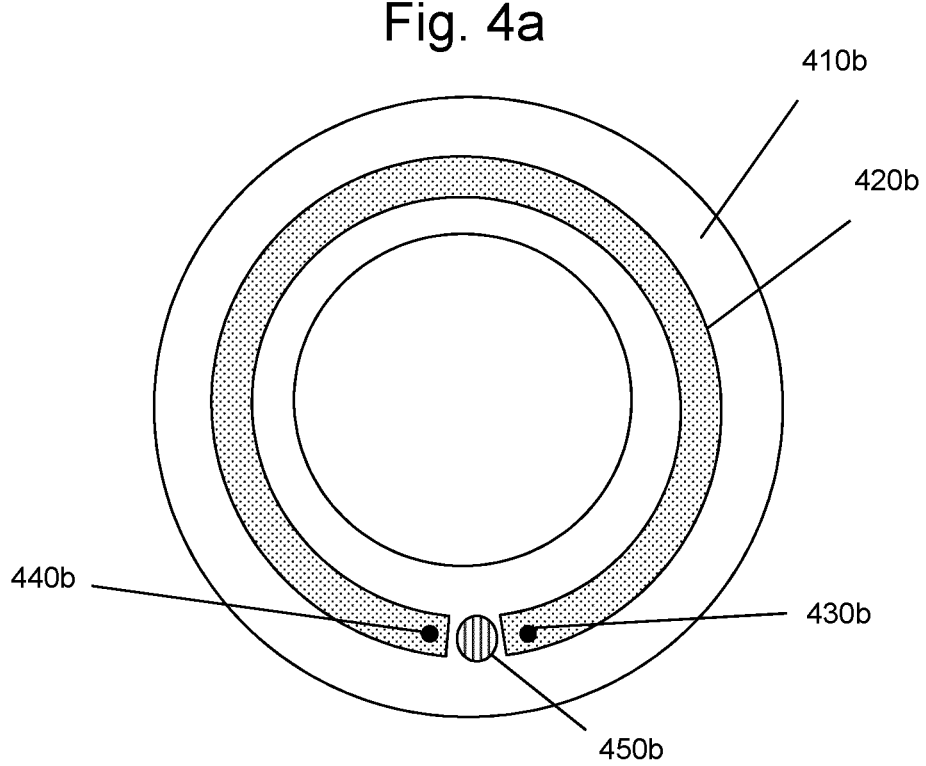

With reference to FIG. 4b, the heat transfer conduit 420b is substantially annular, e.g. substantially ring-shaped. The ring shape shown in FIG. 4b sweeps out over 270 degrees of arc, and in a preferred embodiment the substantially annular conduit 420b may sweep out over 300 degrees of arc. The implementation shown in FIG. 4b also comprises a grease fitting or grease nipple 450b. The grease fitting or nipple facilitates the application of a thermally conductive lubricant to the face of the heat transfer conduit 420b. In an embodiment in which the first and second conduit are in direct physical contact, the grease fitting 450b facilitates the reduction of friction between the first and second conduit as the first conduit slides against the second conduit as the gantry rotates.

In a disclosed implementation, the arrangement depicted in FIG. 4a forms part of the on-gantry heat transfer system, while the arrangement depicted in FIG. 4b forms part of the off-gantry heat transfer system. The thermally conductive surface of the heat transfer conduit 420a forms an interface with the thermally conductive surface of the heat transfer conduit 420b. In some implementations, there is direct contact between the heat transfer conduit 420a and brush blocks 420c to facilitate heat transfer. As the on-gantry heat transfer system rotates, the first conduit 420a slides against the second conduit 420b. Thus, the interface between the on-gantry heat transfer system and the off-gantry heat transfer system forms a sliding joint, in other words there is a sliding interface. Via this interface, heat can be transferred from the on-gantry heat transfer system to the off-gantry heat transfer system in the manner describe generally above. Such an implementation is beneficial because heat is transferred efficiently regardless of gantry angle or speed of rotation.

Figure 4C:
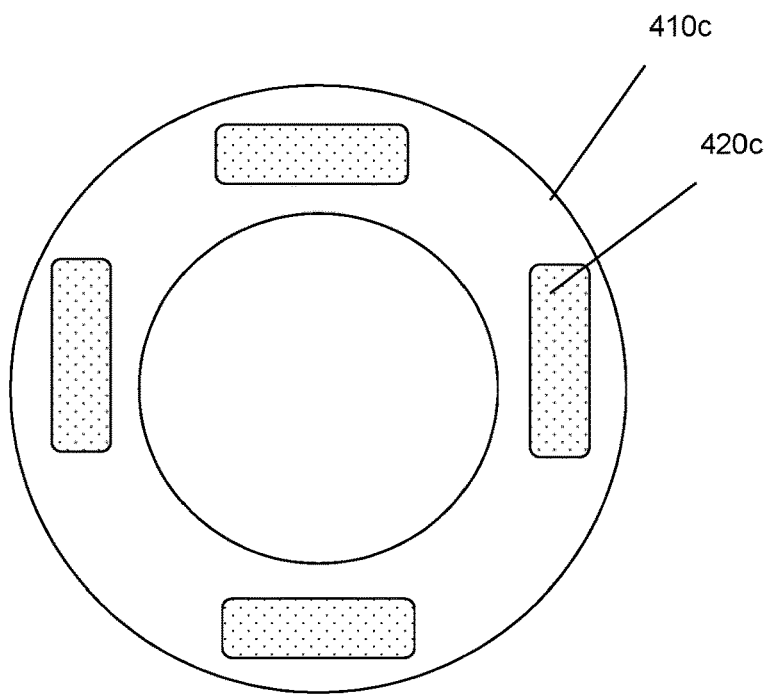
Figure 4D:
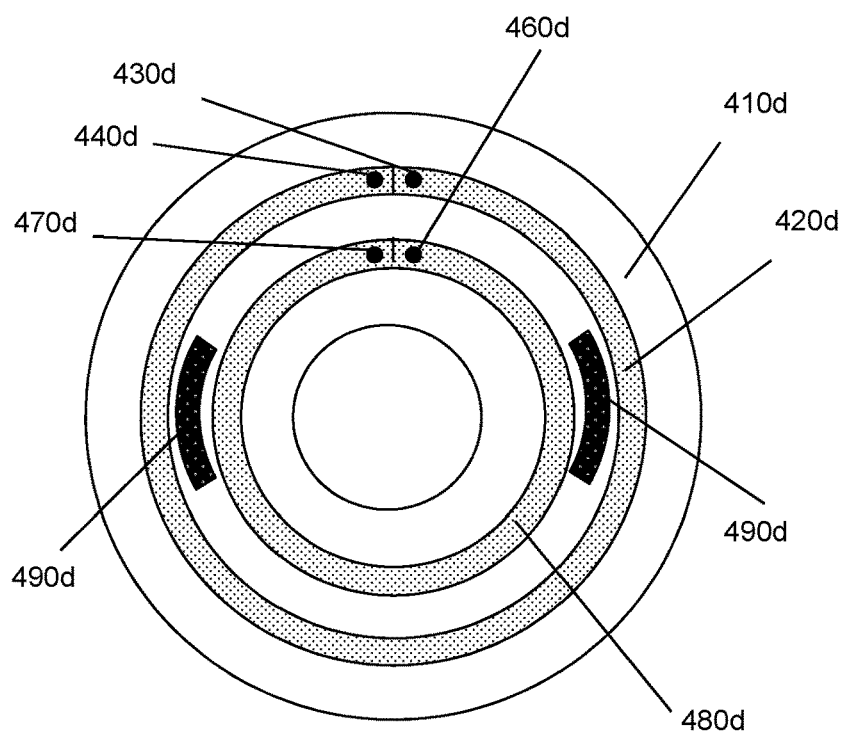
Figure 4E:
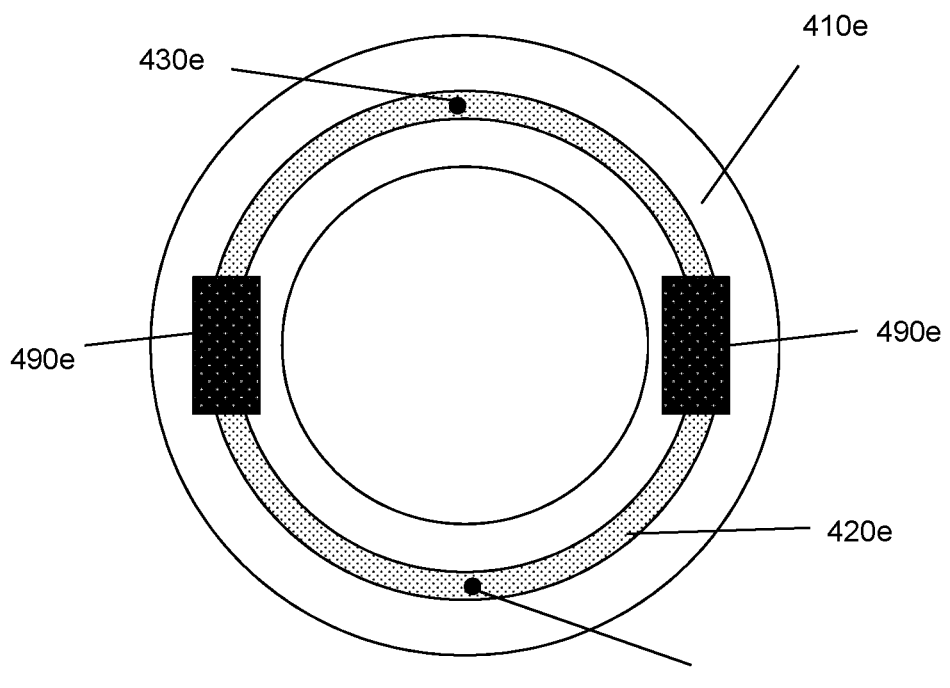

Reference is made to FIG. 4e. As with FIGS. 4a-d, this design could form part of the off-gantry heat transfer system, the on-gantry heat transfer system, or both. In this implementation, the conduit is continuous and the inlet aperture 430e is located substantially 180 degrees from the outlet aperture 440e. As with the other designs shown, fluid is pumped into the conduit via inlet aperture 430e and leaves the conduit via exit aperture 440e.

Heat Transfer Block(s)

Described broadly, the present application relates to an interface formed between a first thermally conductive surface forming part of an on-gantry heat transfer system, and a second thermally conductive surface forming part of an off-gantry heat transfer system. The thermally conductive surfaces may be surfaces of respective conduits or pipes, though they need not be so.

The implementation depicted in FIG. 4c may form part of either the on-gantry heat transfer system or the off-gantry heat transfer system. Taking the off-gantry heat transfer system as an example, the second thermally conductive surface is formed on the face of one or more heat transfer blocks 420c. The blocks may be described as heat transfer elements, or heat transfer shoes. The blocks have a thermally conductive surface which may face the thermally conductive surface of a corresponding brush or heat transfer conduit to form an interface in a manner described generally above. The off-gantry heat transfer system is configured to transfer heat away from the face of the heat transfer block to the fluid cooler 324. For example, a heat transfer conduit may be directed through the one or more blocks 420c so as to transfer heat from, the blocks 420c. The one or more blocks may be cooled or chilled via a conduit which brings chilled or cooled water from the fluid chiller. For example, using disclosed techniques, the blocks used in the off-gantry heat transfer system may be kept at a particular temperature, for example 20 degrees Celsius.

In an implementation in which the configuration of FIG. 4e forms part of the on-gantry heat transfer system, the on-gantry heat transfer system is configured to transfer heat from the beam generating system to the face of the one or more blocks 420c.

In a disclosed implementation, one of the arrangement depicted in FIG. 4a or 4e forms part of the on-gantry heat transfer system, while the arrangement depicted in FIG. 4c forms part of the off-gantry heat transfer system. The thermally conductive surface of the heat transfer conduit 420a forms an interface with the thermally conductive surface of the one or more blocks 420c. In some implementations, there is direct contact between the heat transfer conduit 420a and blocks 420c to facilitate heat transfer. As the on-gantry heat transfer system rotates, the heat transfer conduit 420a slides against the one or more blocks 420c. Thus, the interface between the on-gantry heat transfer system and the off-gantry heat transfer system forms a sliding joint, or sliding interface. Via this interface, heat can be transferred from the on-gantry heat transfer system to the off-gantry heat transfer system in the manner describe generally above.

Multiple Tracks

FIG. 4d shows an arrangement comprising multiple tracks. Reference has been made herein to a first conduit comprised within an on gantry heat transfer system transferring heat to a corresponding second conduit comprised within an off-gantry heat transfer system. However, in some implementations of the present disclosure, there are multiple corresponding conduits which form separate and discrete heat exchanging interfaces. The arrangement of FIG. 4d shows such an implementation. When both the on- and the off-gantry heat transfer systems comprise arrangements as depicted in FIG. 4d, the on-gantry heat transfer system comprises a first and a third thermally conductive surface, and the off-gantry heat transfer system comprises a second and a fourth thermally conductive surface. The first thermally conductive surface is in thermal contact with the second thermally conductive surface to form a first interface between the on-gantry heat transfer system and the off-gantry heat transfer system, and the third thermally conductive surface is in thermal contact with the fourth thermally conductive surface to form a second interface between the on-gantry heat transfer system and the off-gantry heat transfer system.

In a disclosed implementation, the conduit arrangement depicted in FIG. 4d forms part of an on-gantry heat transfer system, while the off-gantry heat transfer system comprises a corresponding conduit arrangement which is also in line with the arrangement depicted in FIG. 4d. Hot water from the on-gantry heat transfer system is circulated around both a first conduit 420d and a third conduit 480d. Hot water enters the first conduit 420d via aperture 430d and exits via aperture 440d. Hot water enters the third conduit 480d via aperture 460d and exits via aperture 470d.

The corresponding off-gantry conduit arrangement comprises a corresponding configuration to that described above in relation to the on-gantry conduit arrangement, and in particular comprises a second and fourth conduit. The first conduit 420d is arranged and configured to transfer heat to the second conduit, and the third conduit 480d is arranged and configured to transfer heat to the fourth conduit.

In a preferred implementation, the first and third conduits form respective first and second rotor rings. The second rotor ring 480d is located inside the first rotor ring 420d. The first and second rotor rings 420d, 480d are positioned coaxially with one another on the platter 410d. Similarly, the second and fourth conduits form respective first and second stator rings. The second stator ring is located inside the first stator ring. The first and second stator rings are positioned coaxially with one another on the platter. In other words, the first and second rotor rings may be concentric rings, and the first and second stator rings may be concentric rings.

In the depicted implementation in FIG. 4d, the conduits are both ring-shaped, however it should be understood that the first, second, third and fourth conduit may take any of the forms and configurations disclosed herein. While four conduits or 'tracks' are shown such that two different heat exchanging interfaces are formed (the first interface between the first and second conduit, and the second interface between the third and fourth conduit), it should be appreciated that a plurality of tracks/conduits may be provided such that a plurality of heat exchanging interfaces are formed between the on-gantry and off-gantry heat transfer systems.

Alternative Shapes for the Heat Exchanging Pipes

While the first and second conduit have been described primarily as rings, or being substantially ring-shaped, or annular, other shapes and forms may be used. The heat transferring conduits may be U-shaped or substantially U-shaped, or may be horse-shoe shaped, for example.

In some implementations, rather than the heat exchanging interface being formed by ring-shaped heat transfer conduits arranged face-to-face, the first annular conduit may be sized and positioned so as to fit 'inside' the second annular conduit, or vice versa. In other words, the thermally conductive surfaces of each ring, through which heat is transferred, may form part of the outer circumference of an inner ring, and the inner circumference of the other, outer ring.

Air Bearing

While reference has been made primarily to a heat exchanging interface formed via direct physical contact between heat transferring conduits, the interface between the first thermally conductive surface and the second thermally conductive surface may take other forms.

In a disclosed implementation, the interface is a gas bearing. The interface may comprise a gas bearing in that the first and second thermally conductive surfaces are separated via a film of gas which is maintained by a gas bearing. In an example, the faces of each conduit, e.g. the first and second thermally conductive surfaces, are kept apart by a separation distance via the use of an air bearing.

The separation distance is preferably less than 1 mm. In preferred implementations, the separation distance is significantly less than 1 mm, and may be for example less than 10 microns or even less than 1 micron. The smaller the distance, the more efficient the heat transfer between the on-gantry heat transfer system and the off-gantry heat transfer system. The separation distance between the first and second thermally conductive surface may be kept within a particular range by the air bearing; for example, the separation distance may be maintained within 0.1 micron to 10 microns by the air bearing. A particularly preferred separation distance is 5 microns.

While reference is made to an 'air bearing' it will be appreciated that any gas may be used and hence the term 'gas bearing' may be used interchangeably with the term 'air bearing' herein. Such bearings are also known as aerostatic or aerodynamic bearings. In an air bearing, a thin film of gas separates the first and second thermally conductive surfaces, for example a thin film of gas may separate the faces of the first and second conduit. The use of an air bearing in this manner provides a low friction interface between the thermally conductive surfaces. The two surfaces do not touch, thus minimising friction and wear. In such an implementation, the surfaces remain in thermal contact but do not physically contact one another. In such an implementation, one or more air or gas jets are used to 'float' the two faces apart in an air/gas bearing.

In such an implementation, i.e. one comprising an air bearing, the apparatus may further comprise an arrangement of air jets configured and positioned so as to maintain the air bearing. The apparatus may further comprise a compressor and a pressure tank for storing compressed air or other gas, which may be supplied to the air jets so as to maintain the air bearing. The air jets may comprise micro-nozzles or other orifices and apertures which may be supplied with compressed air from the pressure tank.

The gas bearing may be maintained via the use of one or more gas bearing components. These components comprise one or more apertures. Pressurised gas is supplied to the gas bearing component which escapes the gas bearing component through the one or more apertures. The one or more apertures may be located in a porous material.

FIG. 4d depicts a design comprising gas bearing elements 490d. In the figure, the gas bearing elements are located radially outward from the 'inner' ring shaped, or substantially ring-shaped, conduit 480d and radially inward from the 'outer' ring-shaped, or substantially ring-shaped, conduit 420d. In other words, in an implementation comprising a plurality of ring-shaped or substantially ring-shaped conduits, the one or more gas bearing elements 490d may be located in between each of the plurality of rings. At an interface comprising one or more gas bearings 490d in the manner depicted in FIG. 4d, pressurised gas is discharged from the apertures in the gas bearing elements to form a thin film of gas between the thermally conductive surfaces of the on-gantry heat transfer system and the thermally conductive surfaces of the off-gantry heat transfer system. In other words, the first and second interfaces each comprise conduits kept apart via a thin film of gas which is maintained via air bearing elements 490d. Two gas bearing elements 490d are depicted in FIG. 4c. However, there may be any number of gas bearing elements 490 as required by the implementation. The gas bearing element may also be ring-shaped to form a gas bearing ring.

FIG. 4e depicts another implementation comprising air bearing elements 490e. These air bearing elements comprise apertures designed to be located between the thermally conductive surfaces of the on-and -off gantry heat transfer system. The air bearing elements may be designed such that the conduit 410e runs through the gas bearing element 430e. The gas bearing elements 490e operate in the manner described elsewhere herein, i.e. to inject gas into the interface between the on-and off-gantry heat transfer systems so as to maintain a thin film or sheet of gas between the thermally conductive surfaces which form the interface so as to reduce, or eliminate, friction between the surfaces forming the interface.

It should be understood that the air bearing elements depicted in FIGS. 4d and 4e are optional and shown as examples to aid the understanding of the skilled person reading this disclosure. The gas bearing elements are not required for implementations in which the interface comprises direct physical contact between the surfaces.

First and Second Stator Ring Structures

FIG. 5 depicts a design comprising a rotor ring structure 530, a first stator ring structure 520a and a second stator ring structure 520b. The rotor ring structure 530 may comprise an on-gantry heat transfer system as described herein. The first stator ring structure 520a and/or the second stator ring structure 520b may comprise an off-gantry heat transfer system as described herein. The figure depicts a cross-section through the rotor ring structure 530 and the first and second stator ring structures 520a, 520b in a 'top-down' view. Therefore, the components depicted at the top of FIG. 5 correspond to the components depicted at the bottom of FIG. 5 and are part of the same structures shown at the bottom of FIG. 5. A patient support surface 214 suitable for a supporting a patient or subject is disposed between these two portions of the rotor ring structure 530 and the first and second stator ring structures 520a, 520b. In other words, the rotor ring structure 530 and the first and second stator ring structures 520a, 520b form rings around the patient support surface 214.

As used herein, references to a rotor ring structure may be used to refer to an on-gantry ring structure, an outwardly extending ring structure and/or a hot ring structure. This is configured to rotate around the patient support surface 214. As used herein, references to a stator ring structure may be used to refer to an off-gantry ring structure, an inwardly extending ring structure and/or a cold ring structure. This is designed to remain stationary when in use.

While both the first stator ring structure 520a and second stator ring structure 520b are described, in some examples a single stator ring structure may be used. In other words, the system comprises at least one stator ring structure. Preferably, the system comprises two stator ring structures. The first stator ring structure 520a may be disposed adjacent to a first surface of the rotor ring structure 530. The second stator ring structure 520b may be disposed adjacent to a second surface of the rotor ring structure 530. The second surface may be opposite to the first surface.

An air gap 550a may be formed between the rotor ring structure 530 and the first stator ring structure 520a. An air gap 550b may be formed between the rotor ring structure 530 and the second stator ring structure 520b. Each of the surfaces of the rotor ring structure 530 and first and second stator ring structures 520a, 520b adjacent to one of the air gaps 550a, 550b may comprise a thermally conductive surface. The interface between the rotor ring structure 530 and the first stator ring structure 520a comprises the air gap 550a. The interface between the rotor ring structure 530 and the second stator ring structure 520b comprises the air gap 550b. The use of first and second stator ring structures 520a, 520b either side of the rotor ring structure 530 enables force balancing of the air gaps 550a, 550b and provision of a large lifting force via the pressurized air supplied.

The system depicted in FIG. 5 may be force balanced using a ball joint which makes adjustment of the air bearing possible. The rotor ring structure 530 and the first and second stator ring structures 520a, 520b may comprise a porous graphite layer 524 adjacent to the respective air gaps 550a, 550b through which pressurized air is supplied. Alternatively, the pressurized air may be supplied via hole feeds. The first and second rotor ring structures 520a, 520b may be supported by a clamp 560 and pivoting spring devices 565. The pivoting spring devices 565 may allow for small movements of the first and/or second stator ring structures 520a, 520b in order to maintain desired air gaps 550a, 550b. For example, this may ensure that the air gaps 550a, 550b are maintained at approximately 5 microns, or at least that the air gaps 550a, 550b remain greater than 0 microns. The clamp 560 may support the pivoting spring devices 565 in order to localize the forces associated with the spring devices 565 and the air gaps 550a, 550b. These may correspond to or comprise similar features to the biasing means described in relation to FIG. 2. Damping means may be provided to damp vibrations in at least one of the rotor ring structure 530, the first stator ring structure 520a and the second stator ring structure 520b.

The rotor ring structure 530 may comprise one or more hot fluid conduits 535. The one or more hot fluid conduits 535 may be annular or concentric. In operation, at least one on-gantry component 314 may generate heat. This heat may be transferred to fluid disposed within the hot fluid conduits 535. The fluid may comprise water or another suitable fluid as disclosed herein. A pump 312 of the rotor ring structure 530 may be configured to cause the fluid to flow or circulate within the hot fluid conduits 535.

The first stator ring structure 520a may comprise one or more cold fluid conduits 525a. The second stator ring structure 520b may comprise one or more cold fluid conduits 525b. The one or more cold fluid conduits 525a and/or the one or more cold fluid conduits 525b may be annular or concentric. The fluid may comprise water or another suitable fluid as disclosed herein. One or more pumps 322 of the first stator ring structure 520a and/or the second stator ring structure 520b may be configured to cause the fluid to flow or circulate within the cold fluid conduits 525a, 525b. In operation, heat may be transferred from the hot fluid conduits 535 to the cold fluid conduits 525a, 525b. The use of both the first stator ring structure 520a and the second stator ring structure 520b is particularly advantageous since it increases the surface area for heat transfer. In other words, heat may be transferred from the hot fluid conduit 535 to both of the cold fluid conduits 525a, 525b, which may as much as double the rate of heat transfer.

While the above design has been described as using an air gap, it will be appreciated that the double-sided second conduit can be combined with designs disclosed herein that use physical contact, for example physical contact via a lubricant. The double-sided second conduit enables increased heat transfer rates in such designs.

Lubricant Feeds and Drains

FIG. 6a depicts a design comprising a rotor ring structure 630 and a stator ring structure 620. The figure depicts a 'side-on' cross-section through part of the rotor ring structure 630 and the stator ring structure 620, i.e. through an arc of each of the rotor ring structure 630 and the stator ring structure 620. The rotor ring structure 630 may comprise (annular, concentric) hot fluid conduits 635. The stator ring structure 620 may comprise (annular, concentric) cold fluid conduits 625. These components may be configured in a similar manner as described in relation to FIG. 5.

Each of the rotor ring structure 630 and the stator ring structure 620 may be in contact with a lubricant film 650 disposed between the rotor ring structure 630 and the stator ring structure 620. The lubricant film 650 may comprise lubricant with high heat conductivity. The lubricant may comprise oil, grease or water. Use of oil as the lubricant may beneficially provide damping of vibrations between the rotor ring structure 630 and the stator ring structures 620. The stator ring structure 620 may comprise a lubricant feed 660 coupled to the lubricant film 650 and configured to supply lubricant to the lubricant film 650. A pump may be used to supply the lubricant via the lubricant feed 650 under pressure. The lubricant feed 660 may be disposed at one or more points around a circumferential extent of the stator ring structure 630 or may be disposed around part or all of the circumferential extent of the stator ring structure 630.

The rotor ring structure 630 may comprise one or more lubricant drains 670a, 670b coupled to the lubricant film 650. Lubricant from the lubricant film 650 may escape from the region between the rotor ring structure 630 and a stator ring structure 620. According to this design, this lubricant can migrate to and be collected in the one or more lubricant drains 670a, 670b, for example via gravity or centrifugal forces. This enables this lubricant to be captured in order to avoid waste and maintain a clean environment. The lubricant can be fed back to the lubricant feed 660 and reused via a return system. The lubricant drains 670a, 670b may be disposed at one or more points around a circumferential extent of the stator ring structure 630 or may be disposed around part or all of the circumferential extent of the stator ring structure 630.

Alternatively, or in addition, the lubricant can be actively sucked or extracted out under pressure as depicted in FIG. 6b. The design of FIG. 6b is similar to the design of FIG. 6a. However, in the design of FIG. 6b, the stator ring structure 620 may comprise one or more lubricant drains 680a, 680b. These lubricant drains 680a, 680b may be coupled to the lubricant film 650 and may be pressurized so as to cause the lubricant to flow from the lubricant film 650 to the lubricant drains 680a, 680b. Air may also be sucked out via the lubricant drains 680a, 680b. This may enable lubricant to be collected while avoiding excesses of lubricant building up in the lubricant film 650, thereby ensuring that run-off of lubricant is avoided. The lubricant drains 680a, 680b may be disposed at one or more points around a circumferential extent of the stator ring structure 630 or may be disposed around part or all of the circumferential extent of the stator ring structure 630.

The one or more lubricant drains 680a, 680b may be separated spatially from the lubricant feed 660. In some examples, the one or more lubricant drains 680a, 680b may be located at outer edges of the stator ring structure 620 and the lubricant feed 660 may be located at a centre of the stator ring structure 620. For lubricant to flow from the lubricant feed 660 to the lubricant drains 680a, 680b, the lubricant may need to flow along a majority of the lubricant film 650 at the interface between the rotor ring structure 630 and a stator ring structure 620. This may ensure that a desired content and distribution of lubricant in the lubricant film 650 is maintained.

FIG. 7 depicts a method for injecting lubricant in accordance with the present disclosure. The method of FIG. 7 may be performed by a controller communicatively coupled to the lubricant feed 660 or to a pump supplying lubricant to the lubricant feed 660. The controller may be communicatively coupled to one or more sensors configured to determine an amount of friction between the rotor ring structure 630 and a stator ring structure 620 and to transmit a signal indicative of this friction to the controller. The sensors may sense or parameterize this friction based on temperature, temperature change, vibrations or contact. The sensors may be configured to sense one or more of these parameters using a thermometer and/or a piezoelectric component.

In a step 710, the method may comprise receiving a signal indicative of friction at the interface between rotor ring structure 630 and a stator ring structure 620, i.e. at the lubricant film 650. The signal may be transmitted from the sensors to the controller. The signal may be a numerical value, for example a temperature, amplitude or coefficient of friction.

In a step 720, the method may comprise determining if the signal is above a threshold. The determining may be performed by the controller. If the signal is not above the threshold, the method may return to step 710. Additional signals indicative of friction at the interface may be received continuously or at intervals. If the signal is above the threshold, the method may continue to step 730.

In the step 730, the method may comprise injecting lubricant. The controller may transmit instructions to the pump to cause injection of the lubricant. The injection may be of a predetermined amount of lubricant and/or may be of an amount of lubricant calculated based on the signal received at step 710. Alternatively, the injection of lubricant may continue until a signal is received that is below the threshold.

Alternatively, a pump configured to provide a constant or approximately constant flow rate and/or a pump configured to provide a constant or approximately constant pressure may be used. One or both of these pumps may be configured to supply lubricant through lubricant feed 660 continuously or substantially continuously in order to ensure lubrication and separation of the rotor ring structure 630 and a stator ring structure 620.

Control System

The disclosed radiotherapy apparatus may also comprise a control system configured to maintain low friction at the interface. The control system comprises a processor or controller coupled to a computer readable medium which stores computer executable instructions which, when implemented by the processor or controller, cause the processor or controller to perform disclosed methods.

In implementations in which the interface comprised physical contact, the processor may control the application of lubricant at the interface based on an input indicative of friction at the interface. The input indicative of friction at the interface may be received from, for example, the gantry rotation mechanism and/or noise sensors. The processor may control a grease gun or grease application mechanism configured to supply grease (or other lubricant) to the interface via the grease fitting 450. It will be appreciated that the power required to maintain a constant rotation rate of the gantry may change or fluctuate depending on the friction between the surfaces of the on-and-off gantry heat transfer system which are in contact to form the interface. In other words, the current supplied to the gantry rotation mechanism/motor can be taken as an indication of friction at the interface. In a simple disclosed method, the processor monitors the current and/or power supplied to the gantry rotation mechanism and, if a threshold is reached, the processor instructs the grease application mechanism to apply grease/lubricant to the interface via grease fitting 450.

Similarly, in implementations in which the interface comprises a gas bearing, a processor may monitor the current supplied to the gantry rotation mechanism/motor and, if a threshold current is reached, the processor is configured to send control signals which cause the gas bearing elements 490 to discharge more air into the interface.

The above implementations have been described by way of example only, and the described implementations and arrangements are to be considered in all respects only as illustrative and not restrictive. It will be appreciated that variations of the described implementations and arrangements may be made without departing from the scope of the invention.

The invention claimed is:
1. A radiotherapy apparatus comprising:
a rotatable gantry;
a beam generation system, attached to the gantry, configured to generate a beam of therapeutic radiation;
an on-gantry heat transfer system configured to rotate with the gantry, the on-gantry heat transfer system including a first conduit comprising a first thermally conductive surface, wherein the on-gantry heat transfer system is further configured to transfer heat generated by the beam generation system to the first thermally conductive surface;

an off-gantry heat transfer system including a second thermally conductive surface, wherein the off-gantry heat transfer system is configured to transfer heat away from the second thermally conductive surface;

wherein the first thermally conductive surface is in thermal contact with the second thermally conductive surface to form an interface between the on-gantry heat transfer system and the off-gantry heat transfer system, the interface comprising at least one of direct physical contact of at least a portion of the first thermally conductive surface with at least a portion of the second thermally conductive surface, or a gas bearing located between the first thermally conductive surface and the second thermally conductive surface.

2. The apparatus of claim 1, the on-gantry heat transfer system further comprising a pump to pump fluid around the on-gantry heat transfer system and through the first conduit.

3. The apparatus of claim 1, wherein the first thermally conductive surface is configured to rotate with respect to the second thermally conductive surface as the gantry rotates and/or wherein the on-gantry heat transfer system is configured to rotate with respect to the off-gantry heat transfer system.

4. The apparatus of claim 1, wherein at least one of of the first thermally conductive surface or the second thermally conductive surface is substantially annular.

5. The apparatus of claim 1, wherein the first conduit is a rotor ring and a second conduit is a stator ring, wherein the rotor ring is configured to rotate with respect to the stator ring as the gantry rotates.

6. The apparatus of claim 5, wherein the second conduit includes the second thermally conductive surface.

7. The apparatus of claim 5, wherein the on-gantry heat transfer system further comprises a third conduit, the third conduit including a third thermally conductive surface and the off-gantry heat transfer system further comprising a fourth conduit, the fourth conduit including a fourth thermally conductive surface, wherein the third thermally conductive surface is in thermal contact with the fourth thermally conductive surface to form a second interface between the on-gantry heat transfer system and the off-gantry heat transfer system, the second interface comprising at least one of direct physical contact of at least a portion of the third thermally conductive surface with at least a portion of the fourth thermally conductive surface, or a second gas bearing located between the third thermally conductive surface and the fourth thermally conductive surface.

8. The apparatus of claim 7, wherein at least one of the third thermally conductive surface or fourth thermally conductive surface is substantially annular.

9. The apparatus of claim 7, wherein the third conduit is a second rotor ring, and the fourth conduit is a second stator ring, wherein the second rotor ring is configured to rotate with respect to the second stator ring as the gantry rotates.

10. The apparatus of claim 9, wherein the second rotor ring is positioned concentric with and inside the rotor ring, and the second stator ring is positioned concentric with and inside the stator ring.

11. The apparatus of claim 5, wherein the first conduit is comprised within a rotor ring structure and wherein the second conduit is comprised within a stator ring structure.

12. The apparatus of claim 11, wherein the rotor ring structure comprises two or more hot fluid conduits and the stator ring structure comprises two or more cold fluid conduits, and wherein at least one of the hot fluid conduits or the cold fluid conduits are annular.

13. The apparatus of claim 11, wherein the stator ring structure comprises a first stator ring structure located adjacent to a first surface of the rotor ring structure and a second stator ring structure located adjacent to a second surface of the rotor ring structure, wherein the second surface is opposite to the first surface.

14. The apparatus of claim 11, wherein the stator ring structure comprises a lubricant feed configured to supply lubricant to a lubricant film located between the stator ring structure and the rotor ring structure, and wherein at least one of:
the rotor ring structure includes one or more lubricant drains coupled to the lubricant film to collect lubricant from the lubricant film, or the stator ring structure includes one or more lubricant drains coupled to the lubricant film to extract lubricant from the lubricant film under pressure.

15. The apparatus of claim 1, further comprising a biasing mechanism to bias one of the first thermally conductive surface or the second thermally conductive surface toward the other of the first thermally conductive surface or the second thermally conductive surface.

16. The apparatus of claim 1, wherein the interface is a sliding interface.

17. The apparatus of claim 1, further comprising a lubricant applicator to provide a thermally conductive lubricant at the interface.

18. The apparatus of claim 1, wherein the the gas bearing separates at least a portion the first thermally conductive surface from at least a portion of the second thermally conductive surface by a separation distance, wherein the separation distance is less than 1 mm.

19. The apparatus of claim 18, further comprising at least one gas jet to maintain the separation distance.

20. A radiotherapy apparatus comprising:
a rotatable gantry;
a beam generation system, attached to the gantry, configured to generate a beam of therapeutic radiation;
an on-gantry heat transfer system configured to rotate with the gantry, the on-gantry heat transfer system including:
a first conduit comprising a first thermally conductive surface, wherein the on-gantry heat transfer system is further configured to transfer heat generated by the beam generation system to the first thermally conductive surface; and
a pump to pump fluid around the on-gantry heat transfer system and through the first conduit;
an off-gantry heat transfer system including a second thermally conductive surface, wherein the off-gantry heat transfer system is configured to transfer heat away from the second thermally conductive surface; and
a biasing mechanism to bias one of the first thermally conductive surface or the second thermally conductive surface toward the other of the first thermally conductive surface or the second thermally conductive surface;
wherein the first thermally conductive surface is configured to rotate with respect to the second thermally conductive surface, wherein at least one of the first thermally conductive surface or the second thermally conductive surface is substantially annular, wherein the off-gantry heat transfer system comprises a second conduit, wherein the second conduit includes the second thermally conductive surface, wherein the first conduit is a rotor ring and the second conduit is a stator ring, wherein the rotor ring is configured to rotate with respect to the stator ring as the gantry rotates, wherein the first thermally conductive surface is in thermal contact with the second thermally conductive surface to form an interface between the on-gantry heat transfer system and the off-gantry heat transfer system, the interface comprising at least one of direct physical contact of at least a portion of the first thermally conductive surface with at least a portion of the second thermally conductive surface, or a gas bearing located between the first thermally conductive surface and the second thermally conductive surface.

\* \* \* \* \*